(12) United States Patent
Mirza et al.

(10) Patent No.: US 11,026,701 B1
(45) Date of Patent: Jun. 8, 2021

(54) SYSTEM AND METHOD FOR FORMING A CAVITY IN SOFT TISSUE AND BONE

(71) Applicant: Dartmouth-Hitchcock Clinic, Lebanon, NH (US)

(72) Inventors: Sohail K. Mirza, Hanover, NH (US); Keith D. Paulsen, Lebanon, NH (US); Ryan J. Halter, Orford, NH (US)

(73) Assignee: Dartmouth-Hitchcock Clinic, Lebanon, NH (US)

( * ) Notice: Subject to any disclaimer, the term of this patent is extended or adjusted under 35 U.S.C. 154(b) by 567 days.

(21) Appl. No.: 15/469,461

(22) Filed: Mar. 24, 2017

Related U.S. Application Data

(60) Provisional application No. 62/313,651, filed on Mar. 25, 2016.

(51) Int. Cl.
*A61B 17/00* (2006.01)
*A61B 17/16* (2006.01)

(52) U.S. Cl.
CPC ...... *A61B 17/1628* (2013.01); *A61B 17/1626* (2013.01); *A61B 2217/007* (2013.01); *A61B 2562/00* (2013.01)

(58) Field of Classification Search
CPC combination set(s) only.
See application file for complete search history.

(56) References Cited

U.S. PATENT DOCUMENTS

| | | | |
|---|---|---|---|
| 5,928,239 A | 7/1999 | Mirza | |
| 6,358,251 B1 | 3/2002 | Mirza | |
| 2011/0245833 A1* | 10/2011 | Anderson | A61B 17/1626 606/80 |
| 2013/0092441 A1* | 4/2013 | Hummes | E21B 17/07 175/56 |
| 2014/0148808 A1* | 5/2014 | Inkpen et al. | G01B 7/003 606/80 |

* cited by examiner

*Primary Examiner* — Sameh R Boles
(74) *Attorney, Agent, or Firm* — Loginov & Associates, PLLC; William A. Loginov (57) ABSTRACT

A system and method for creating a cavity with a drill assembly provides a powered drill shaft assembly having an articulating tip and a position sensor along the drill shaft; a drill motor assembly with a rotational motor, linear actuator, torque sensor, rotation sensor, electrical resistance sensor and a controller unit having a plurality of programs providing user interface and controlling the operation of the powered drill arrangement; a shroud for the drill shaft with a water port; and a computer software package that combines user specifications with sensor data to control activation and displacement of the drill with a user interface, controls the motor for rotational speed and drilling depth, and gives sensor status, and a display displaying status of a drilling procedure and an image from an imaging device, and that is programmable for a set of parameters for a drilling procedure.

14 Claims, 5 Drawing Sheets

SYSTEM AND METHOD FOR FORMING A CAVITY IN SOFT TISSUE AND BONE

RELATED APPLICATIONS

This application claims the benefit of U.S. Provisional Application Ser. No. 62/313,651, filed Mar. 25, 2016, entitled SMART CAVITY CREATOR DRILL, the entire disclosure of which is herein incorporated by reference.

FIELD OF THE INVENTION

This invention relates to a device and method of forming a cavity in soft tissue or bone in a minimally invasive manner and more particularly, to form an internal cavity having a radius greater than that of the insertion opening.

BACKGROUND OF THE INVENTION

Minimizing harm to patients during medical treatment has been a guiding principle of physicians since the days of Hippocrates. For surgeons, this principle has meant minimizing the surgical injury to the patient during procedures while at the same time, achieving the surgical goals. Some practical applications of this principle have achieved new levels of success with the technological advancements of minimally invasive surgery. Techniques using indirect and direct visualization methods allow performance of surgical work through small openings. These techniques have been refined to successful clinical applications, particularly over the past ten years. Orthopedic, gynecologic, and thoracoabdominal surgical techniques have been revolutionized by progress in minimally invasive surgical techniques. Minimally invasive techniques are also used in neurosurgical procedures to minimize surgical injury to critical neural tissues. Additionally, techniques have been developed to allow percutaneous removal of intervertebral discs.

There are two types of bone tissue: cortical bone and cancellous bone. Cortical bone is synonymous with compact bone, and cancellous bone is synonymous with trabecular and spongy bone. Cortical bone forms the extremely hard exterior while cancellous bone fills the hollow interior. The tissues are biologically similar; the difference is in how the microstructure is arranged. Thus, the exterior formation of a bone is denser than its softer center.

One example of a procedure upon a bone is percutaneous vertebroplasty, a newer technique in which a medical grade cement can be injected though a needle into a painful fractured vertebral body. This stabilizes the fracture, allowing most patients to discontinue or significantly decrease analgesics and resume normal activity. A surgeon can use a drill to create an entry hole and hollow out an interior cavity within a preselected bone. The removed bone can be liquefied and withdrawn by irrigation. The created cavity can then be filled with the cement. There is a risk of unintended damage due to misalignment of the drill bit and other factors. Given that the vertebrae are part of the spinal column, inaccuracies in the procedure can lead to catastrophic problems for the patient.

It would be desirable to provide a system and method for creating a cavity within a bone using a controlled drill bit that is precisely guided to create a cavity that is of desired dimensions and a mechanism for anchoring the drill assembly for a precise result.

SUMMARY OF THE INVENTION

The present invention overcomes the disadvantages of the prior art by providing a system and method forming a cavity in soft tissue and bone using a drill assembly that includes a powered drill for creating a cavity of desired dimensions. The drill can include a drill shaft assembly; and a drill motor assembly including a plurality of sensors and a controller unit providing guidance as to rotational speed, motion and depth. The drill shaft assembly can include a drill shaft with an articulating tip that can pivot in a radial arc from a first position that is oriented to a longitudinal axis that is drawn along the shaft to a second position that can be oriented to a perpendicular axis that is perpendicular to the longitudinal axis, and a position sensor positioned at a place along the drill shaft. The drill motor assembly can include at least one rotational motor that rotationally drives the drill shaft with a rotational spin and at least one linear actuator that provides a back and forth movement of the drill shaft. The drill motor assembly can also include at least one torque sensor, at least one rotation sensor, and at least one electrical resistance sensor. The drill motor assembly can include at least one programmable controller unit that includes a plurality of programs that provide a user interface and control the functions and operations of the powered drill arrangement. The drill can include a shroud for the drill shaft that can include a port for insertion of water that can be pressurized by an external pump for irrigation and removal of deconstructed bone and marrow material from the cavity created by a drilling procedure. A computer software package can combine user specifications with sensor data to control activation and displacement of the drill. The drill can include a computer software package that provides a user interface, controls drill shaft rotational speed and/or drilling depth. The computer software package can collect and report the status of at least one of a position sensor, a torque sensor, a rotation sensor or an electrical sensor. The computer software package can include a display that displays status of a drilling procedure and an image from an imaging device that is oriented at a region around a drilling entry point in a bone. The computer software package can be programmable for a set of parameters for a drilling procedure and can guide the operation of the drill during the drilling procedure. An anchoring device assembly for a powered drill for creating a cavity of desired dimensions in a bone, the anchoring device anchored to at least one of a nearby bone or a nearby area on the same bone, and the anchoring device including a multi-directional bearing that is guidable in multiple degrees of freedom. The anchoring device assembly can include a cannula drill guide assembly; a spherical bearing assembly; and a base assembly. The cannula drill guide assembly can include a hollow tube that receives an inserted drill member. The spherical bearing assembly can include a spherical bearing that is constructed with a through hole that is sized to receive and contain the cannula drill guide. The spherical bearing assembly can include an outer ring with a locking set screw that can be mounted in the outer ring and that can lock the spherical bearing in a desired orientation. The base assembly can include a pivot mounting; an X-Y stage; and/or a guide housing. The anchoring device can include a base assembly that can include a pivot mounting that can attach the spherical bearing assembly and cannula drilling guide assembly to a X-Y stage. The X-Y stage can be a calibration device and that can rotate through multiple directions and can position the spherical bearing assembly with an attached power drill. The anchoring device can include a guide housing that can be a mounting interface and can include at least two mounting screw holes. The mounting screw holes can be for retaining screws that secure the anchoring device assembly to at least one vertebra. A method for creating a cavity within a selected vertebra for a percutaneous vertebroplasty procedure using a drill assembly according to an embodiment herein can include preparing the location for mounting the anchoring device assembly by creating holes for receiving mounting screws in at least one anchoring vertebrae adjacent to the selected vertebra; placing the anchoring device assembly onto the at least one adjacent anchoring vertebrae and inserting mounting screws through screw holes in a mounting guide and tightening the mounting screws; using a tracking device to orient and position a cannula drill guide assembly towards an intended entry point by determining and implementing the desired x, y and z-axis settings in an X-Y stage; tightening a locking set screw to secure the spherical bearing in place when the cannula drill guide is satisfactorily positioned; mounting a drill assembly onto the anchoring device assembly by inserting a drill shaft assembly into the cannula drill guide until a distal tip of a drill shaft assembly is in proximity to the intended entry point; programming a set of parameters for a cavity creation procedure into a computer software package of a computer device; connecting the drill assembly to a power source, a source of pressurized water; placing an imager so that a field of view of the imager is focused at an entry point and a region surrounding the entry point; establishing communication between the imager and the computer software package; activating the computer software package to conduct a drilling procedure to create a cavity according to a set of pre-programmed parameters; observing and evaluating a progress of a drilling procedure to create a cavity using displayed images from the imager and feedback readings from various related sensors on a display; and removing the drill assembly and anchoring device assembly.

BRIEF DESCRIPTION OF THE DRAWINGS

The invention description below refers to the accompanying drawings, of which.

DETAILED DESCRIPTION

Figure 1:
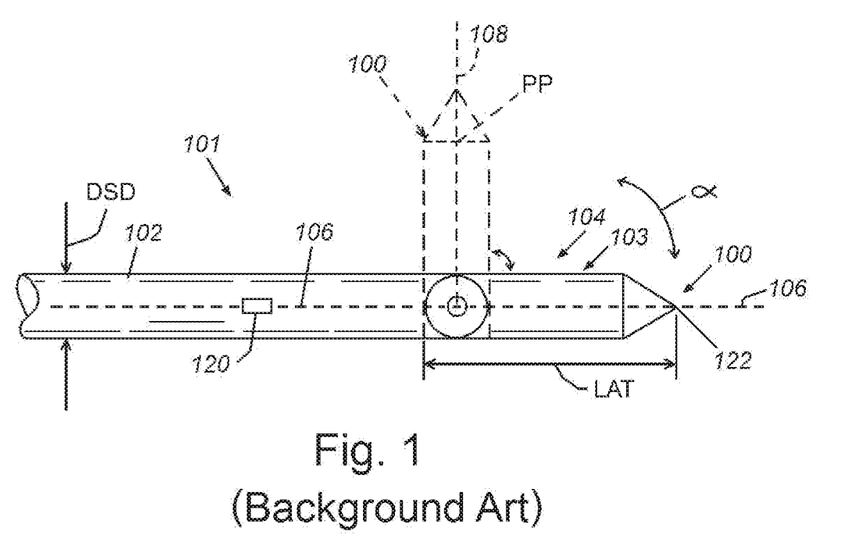
FIG. 1 is a view of a distal end of a drill, according to the background art.

FIG. 1 is a view of a distal end of a drill, according to the background art. A powered drill can include an electric motor, and a drill shaft assembly 100 that can include a drill shaft 102 that is provided with an articulating tip and a plurality of sensors. A distal end 103 of the drill shaft 102 can include an articulating tip 104 that can have a distal tip 122, as shown in FIG. 1, according to the background art. The articulating tip 104 can be capable of movement describing an angle α of up to 90 degrees from a first position oriented to a longitudinal axis 106 that is drawn along the shaft 102 to a second position oriented to a perpendicular axis 108 that is perpendicular to the longitudinal axis 106. The pivoting motion can be activated by the rotational movement of the drill shaft reaching a threshold speed. As the rotational speed increases, the tip's movement can describe an arc. Above a certain threshold of rotational speed, the tip can move into the perpendicular configuration oriented along the perpendicular axis 108. In an embodiment, the threshold rotational speed to achieve a perpendicular orientation can be approximately 20,000 rpm (±500 rpm). The electric motor (not shown) can include computer guided controls, a torque sensor, an electrical resistance sensor and can be programmable. The drill shaft assembly 100 can be displaced forward and backward along the longitudinal axis 106 by operation of a linear actuator (not shown) and can be provided with a position and orientation sensor 120 that can be mounted at a position along the shaft 102. In the illustrative embodiment, the diameter of the drill shaft 102 (DSD) can be 4 mm and the length of the articulating tip 104 (LAT) can be 8 mm, resulting in a cavity diameter of up to 16 mm when the articulating tip 104 is fully perpendicular with respect to the longitudinal axis 106. In other embodiments, drill shaft assemblies can be provided with a greater or lesser thickness, and/or with articulating tips of greater or lesser length. A position sensor 120 can be located at a point along the drill shaft 104 that can report the position of the drill shaft relative to the drill to a controller (described more fully below). As used herein the directional terms, such as, but not limited to, "up" and "down", "upward" and "downward", "rear", "rearward" and "forward", "top" and "bottom", "inside" and "outer", "front" and "back", "inner" and "outer", "interior" and "exterior", "downward" and "upward", "horizontal" and "vertical" should be taken as relative conventions only, rather than absolute indications of orientation or direction with respect to a direction of the force of gravity.

In operation, a drill motor can rotationally drive the drill shaft with a rotational spin and a linear actuator can provide a back and forth movement of the drill shaft assembly for greater or lesser depth. In practice, it has been observed that a rotating drill shaft having a diameter DSD of 4 mm and a articulating tip with a length (LAT) of 8 mm can cause the articulating tip to shift through an angle of movement α, during which the distal tip end 103 can move to the perpendicular position (PP) at approximately 20,000 rpm for the rotation speed. This movement can create a cavity that is bell-shaped. By alternating drill shafts with articulating tips of different lengths (LAT), a mushroom-shaped cavity can be created, as shown in FIG. 2 of the background art.

Figure 2:
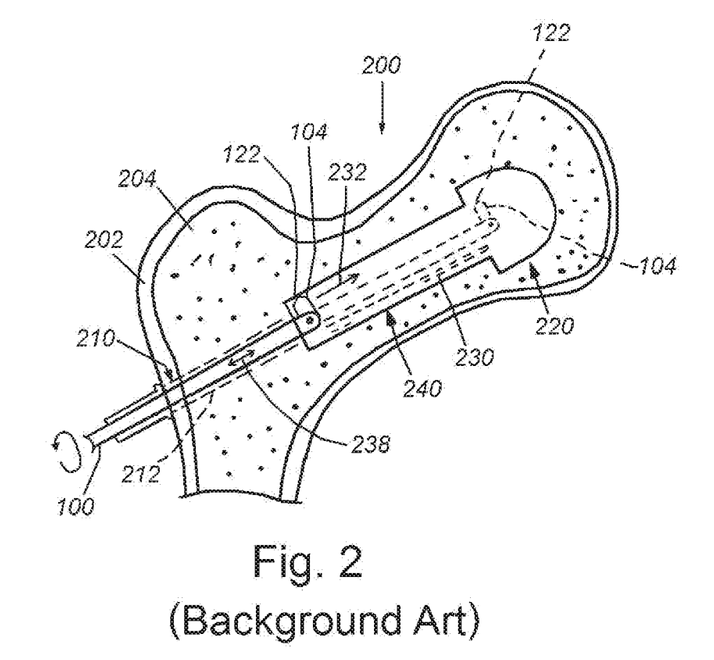
FIG. 2 is partial cut-away view of a femur with an inserted drill, according to the background art.

FIG. 2 is partial cut-away view of a femur with an inserted drill, according to the background art. FIG. 2 shows a partial cut-away view of a proximal femur 200 with avascular necrosis that is being prepared for a cavity for introduction of medical concrete to support and stabilize a hip joint. An entry hole 210 can be drilled through the denser layer of cortical bone tissue 202 into the softer cancellous bone tissue 204 to a requisite depth. A drill shaft assembly 100 can then be inserted to the desired length and the head of the cavity 220 can be created through excavation by increasing the speed of rotation of the drill shaft assembly 100 until the articulating tip 104 can begin to move through an arc from the longitudinal axis 106 to the perpendicular axis 108 and assumes the perpendicular position PP. While the drill is rotating, bone can be removed by the distal tip 122. The deconstructed (e.g., liquefied) bone and marrow material 230 can be removed from the newly excavated cavity by the forced introduction of pressurized water 232 for irrigation. The pressurized water 232 can be pressurized from an exterior pump (not shown) along the drill shaft from the entry hole 210 into the cavity and can force the deconstructed bone material 230 to flow back towards the entry hole, where it can be picked up by suction (not shown). When the operator changes drill shafts to a drill shaft with one of a lesser length articulating tip, a cylindrical cavity with a decreased diameter can be produced. The linear actuator can move the drill shaft back and forth along arrow 238 to create an elongated tunnel 240, resulting in the desired mushroom-shaped cavity that mimics the ball and shaft shape of the original hip bone and optimizes the results for the concrete when introduced through the entry hole. The back and forth movement range can be, by way of non-limiting example, approximately 10 mm (+2 mm), depending on the size and shape of the femur 200 and the desired cavity 240. The excavation process can be observed and evaluated by imaging technology, for example, by fluoroscopy. The actual control of the rotation speed and linear movement of the drill shaft can be computer driven.

Figure 3:
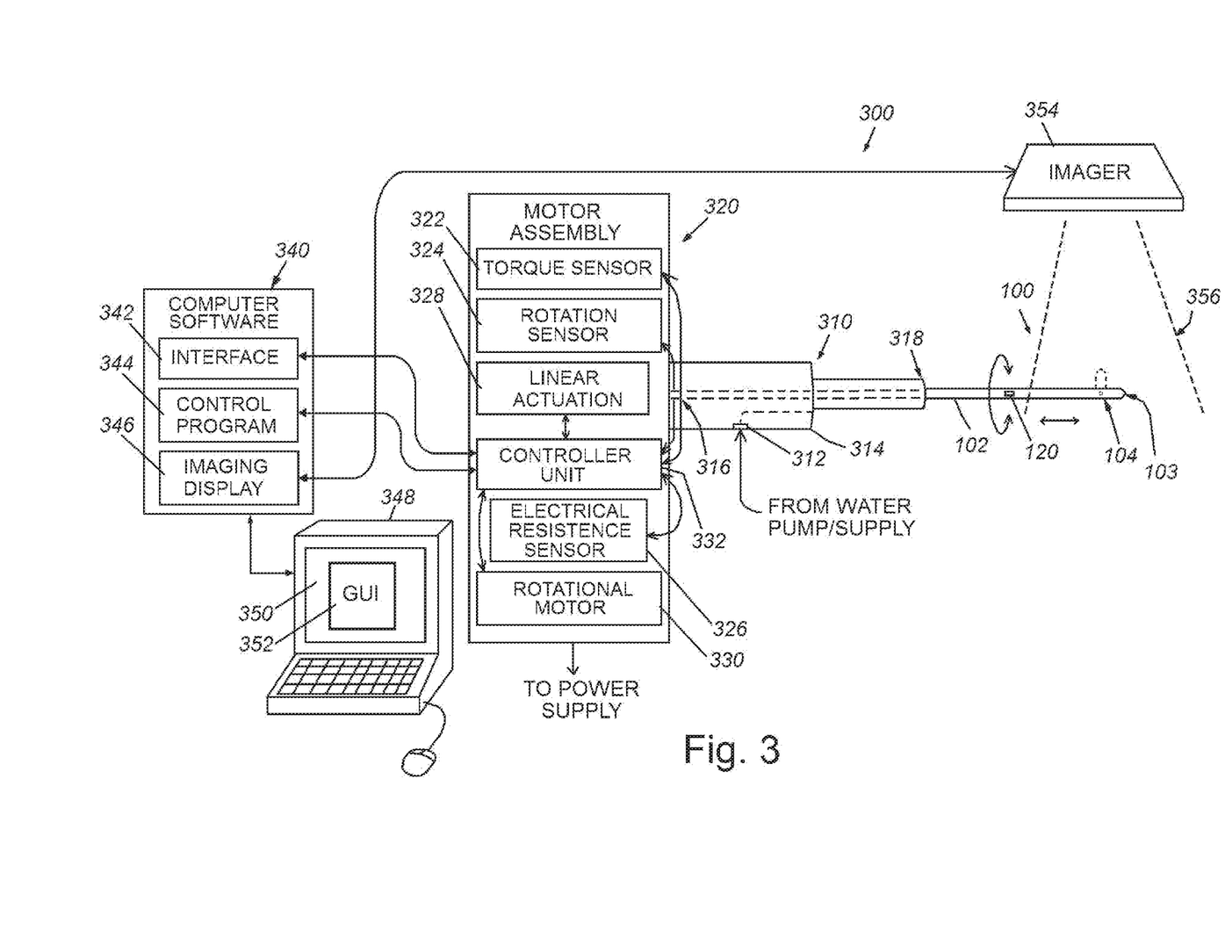
FIG. 3 is a generalized overview of a powered drill arrangement according to an illustrative embodiment.

FIG. 3 details a generalized overview of a powered drill arrangement 300, according to an illustrative embodiment. The depicted exemplary arrangement 300 includes a drill shaft assembly 100 having a drill shaft 102 that can have an articulated tip 104, a handle shroud assembly 310 and a motor assembly 320. The handle shroud assembly 310 can include a port 312 at a point along its exterior surface 314 for attachment to a water source with a pump for removal of deconstructed (e.g., liquefied) bone and marrow material (described above). The drill shaft assembly 100 can be attached to the motor assembly 320 at its proximal end 316 and can pass through an interior space within the handle shroud assembly 310, emerging from the distal end 318 of the handle shroud assembly. In another embodiment, the motor assembly can be an add-on accessory to the drill arrangement, using a commercially available motor that attaches on to the drill assembly.

The motor assembly 320 can include sensors, motors and related applications. The sensors can include a torque sensor 322, a rotation sensor 324 and an electrical resistance sensor 326. The torque sensor 322 can measure and record the torque of the rotational motor. The rotation sensor 324 can measure and record the rotation of the drill shaft assembly. The electrical resistance sensor 326 can measure the resistance or conductance of the electrical components of the motor assembly. With respect to the motors, there can be a linear actuator 328 and there can be a rotational motor 330. The linear actuator 328 can be an actuator that creates motion in a straight line, moving the drill shaft assembly back and forth. The linear actuator can be constructed to create the motion with a hydraulic device, a pneumatic device, a screw drive or a similar device. It is contemplated that in various embodiments, a hydraulic device can be actuated using water, oil or air. The rotational motor 330 can be, by way of non-limiting example, an electric motor that causes the drill shaft assembly to rotate at a desired speed (described as revolutions per minute, rpm).

A programmable controller unit 332 can control and guide the various devices of the motor assembly. The term "controller" should be taken broadly to include a variety of electronic hardware and/or software based functions and components. Moreover, a depicted controller can be combined with other processes and/or processors or divided into various sub-processes or processors. Such sub-processes and/or sub-processors can be variously combined according to embodiments herein. Likewise, it is expressly contemplated that any function, process and/or processor herein can be implemented using electronic hardware, software consisting of a non-transitory computer-readable medium of program instructions, or a combination of hardware and software. The controller unit 332 can be in communication with the torque sensor 322, position sensor 120, rotation sensor 324 and electrical resistance sensor 326 and can receive information and feedback from each of those sensors. Likewise, the controller unit 332 can be in communication with the linear actuator 328 and rotational motor 330, and can both receive feedback from those motors and instruct each of them as to initiating and terminating motions and extent of movement and/or speed of movement (and rotation).

The controller unit 332 can be guided by a computer software package 340 that can include a plurality of programs that provide a user interface and control the functions and operation of the powered drill arrangement 300. The programs and sub-programs of the computer software assembly 340 can include programs for a user interface 342, a control program 344 that controls the controller unit 332 of the motor assembly 320, including rotational speed and drilling depth, an imaging display 346 and other related programs. The computer software package can be contained within a general purpose, or dedicated, computing device 348, such as a PC, laptop, tablet or smartphone. The computing device can include a user interface that can be a keyboard, touch screen or similar device, and a display 350 that can include a graphic user interface screen 352. In practice, a user can input instructions for a procedure through the user interface 342 into the computer software package 340. The programs and/or sub-programs can then process the instructions and provide information to the motor assembly 320 that can in turn activate the drill shaft assembly and can create a cavity to the desired dimensions. The progress of the procedure can be monitored by the user on the display 350 that can show images from an imager 354 that can be viewing the procedure within a field of view 356. The connections between the imager 354, the computing device 348 with the computer software package 340, various sensors and the powered drill can be wired or wireless, either directly linked or indirectly linked. The motor assembly 320 can be attached to an external power supply by a cord or to a battery power supply that can be independent of a wired power supply.

Figure 4:
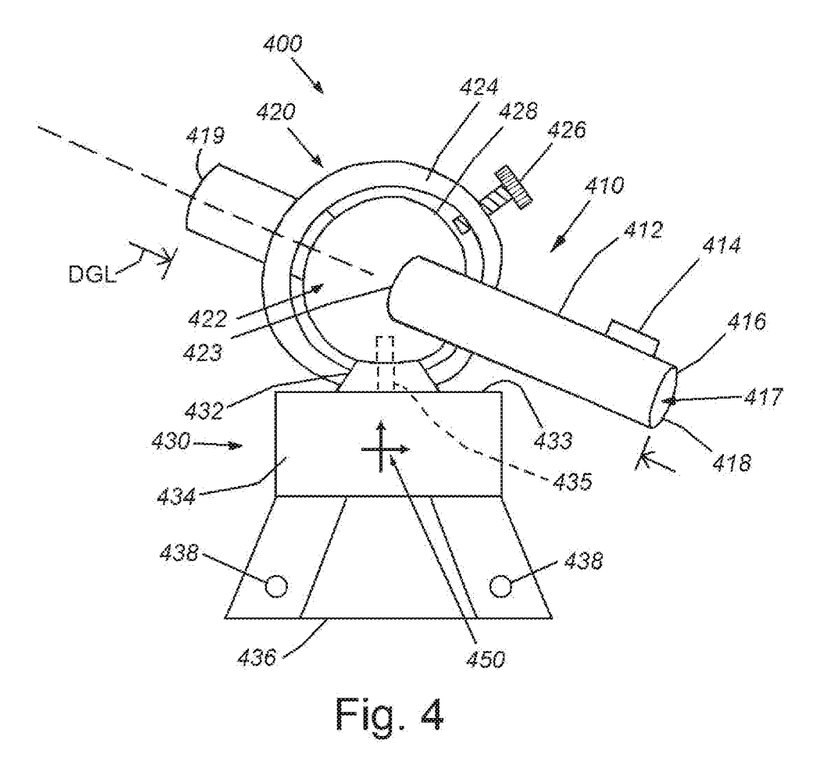
FIG. 4 is a view of an anchoring device assembly according to an illustrative embodiment.

FIG. 4 is a view of an anchoring device assembly according to an illustrative embodiment. To improve the process of creating a cavity in bone for percutaneous vertebroplasty, where nerve damage and bone damage are potential risks, it is desirable to properly stabilize the drill so that the drill shaft can be precisely guided and the surgical outcome can be more predictable, thus increasing the efficacy of the procedure. An anchoring device assembly 400 for the drill assembly can be a device that provides a stable platform for the drill during operation procedures. It is a temporary device that can be emplaced as preparation for the drilling and cement insertion and removed after those procedures have been completed. An exemplary anchoring device 400 is shown in FIG. 4 and can include a cannula drill guide assembly 410, a bearing assembly 420 and a base assembly 430. The cannula drill guide assembly 410 can include a cannula drill guide 412 and a tracking device 414. The tracking device 414 can be an optical device, electromagnetic device or another mechanism that can be used in adjusting the position and orientation of the drill shaft (not shown). The cannula drill guide 412 can be a hollow tube with an outer wall 416 and the inner channel 417 that is a void space surrounded by the outer wall. The tracking device 414 can be mounted at a point along the outer wall 416. The inner channel 417 can receive an inserted shaft (not shown) at the proximal end 418. The channel can be sized to receive a drill shaft of the inserted drill or the drill shaft and shroud of the inserted drill. The inserted shaft can pass through the inner channel 417 and emerge at the distal end 419. The shaft fits within the cannula drill guide and can be sized to have a snug fit along the length of the inner channel of the drill guide. It is contemplated that the cannula drill guide can be provided with a locking mechanism that secures the shaft when inserted that can be activated directly (manually) or indirectly (via wired or wireless communication to the computer device (not shown). The overall length (DGL) of the cannula drill guide 412 can be, by way of non-limiting example, approximately 70 mm (±5 mm). It is contemplated that in other embodiments, this length can be greater or lesser.

The bearing assembly 420 can include a spherical bearing 422, an outer ring 424 and a set screw 426. The spherical bearing 422 can be constructed with a through hole 423 that passes through the bearing and can be sized to receive and contain the cannula drill guide 412. The spherical bearing 422 can be a multi-dimensional bearing and can be guidable in multiple degrees of freedom. The outer ring 424 can be anchored to the pivot mounting 432. A locking set screw 426 can be threaded through the outer ring 424 and can locks the spherical bearing 422 in a desired orientation (as will be more fully described below). The locking set screw 426 can prevent rotation or displacement of the spherical bearing and of the cannula drill guide.

The base assembly 430 can include a pivot mounting 432, a X-Y stage 434 and a guide housing 436. The pivot mounting 432 can be set within the X-Y stage 434 at the top surface 433 of the X-Y stage. The guide housing 436 can be a mounting interface that can include at least two mounting screw holes 438. The mounting holes 438 can be sized to receive at least two screws (not shown). The anchoring device assembly 400 can be temporarily fixed to at least one bone, such as the two vertebrae adjacent to the vertebra that is the object of the procedure, and can be fixed to the bone by screws that can be inserted through the mounting screw holes 438, as will be more fully described below.

The X-Y stage 434 is a calibration device that can rotate and position the spherical bearing assembly 420 that can guide a powered drill. The adjustment can be a manually operated motion slide with adjustment to the x and y axis or can be computer driven. Adjustment to the Z-axis can be performed through movement of the spherical bearing 422. In another embodiment, it is contemplated that the pivot can be replaced by a different bearing with limited rotational movement and the adjustment of the X-Y stage can include adjustment of the X-axis, the Y-axis, and the Z-axis.

Figure 5:
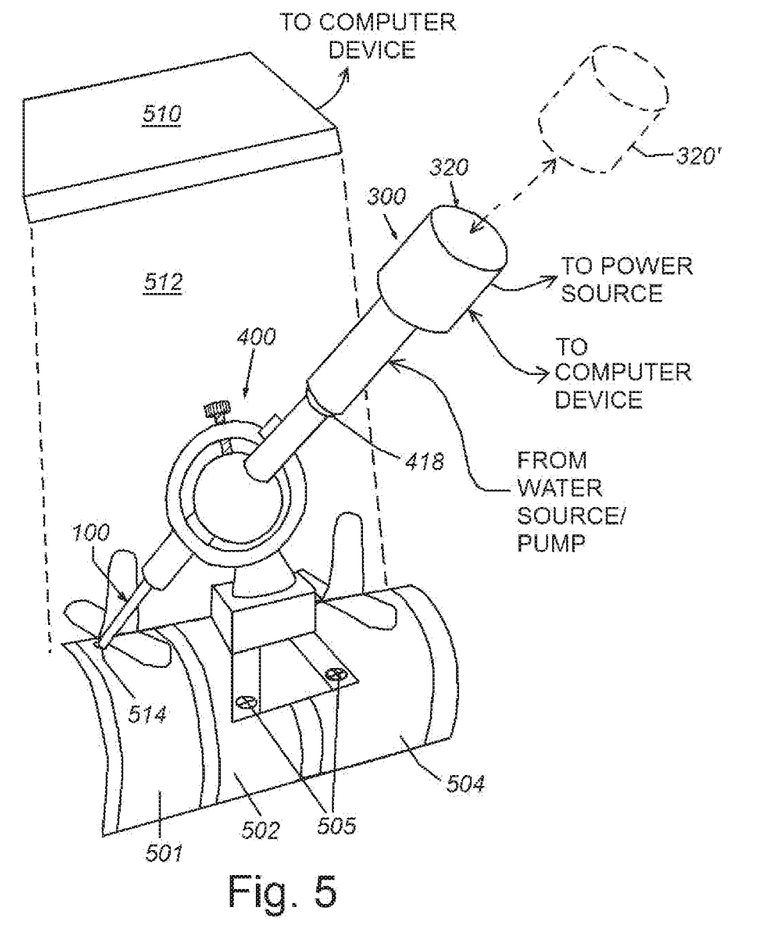
FIG. 5 is a view of an anchoring device assembly mounted for a procedure according to the illustrative embodiment.

FIG. 5 is a view of an anchoring device assembly mounted for a procedure according to the illustrative embodiment. A drilling procedure can be performed on a vertebra 501 as part of a cavity creation for a percutaneous vertebroplasty. The power drill assembly 300 can be mounted to an anchoring device assembly 400 that can be mounted on two vertebrae 502, 504 using mounting screws 505. This creates a secure fitment for the anchoring device assembly that will reduce unintended wobbling or vibration of the drilling device during the procedure. The progress of the procedure can be evaluated by an imager device 510 with a field of view 512 that is directed to vertebra 501. The typical cavitation of a vertebral body can be accomplished in three to four back-and-forth passes and a total of 30 to 40 seconds of drill time per level. The drill shaft assembly 100 enters the vertebra at an entry point 514. The cavity thus created can be 'smart' in the sense that it can be created using a computer guided power drill and can be precisely created to desired dimensions for optimal efficacy in the outcome. In the illustrative embodiment, the motor assembly 320 is shown as an integral part of the power drill assembly 300. It is contemplated that in another embodiment, the motor assembly 320' can be attachable and detachable, as depicted in broken lines.

Figure 6:
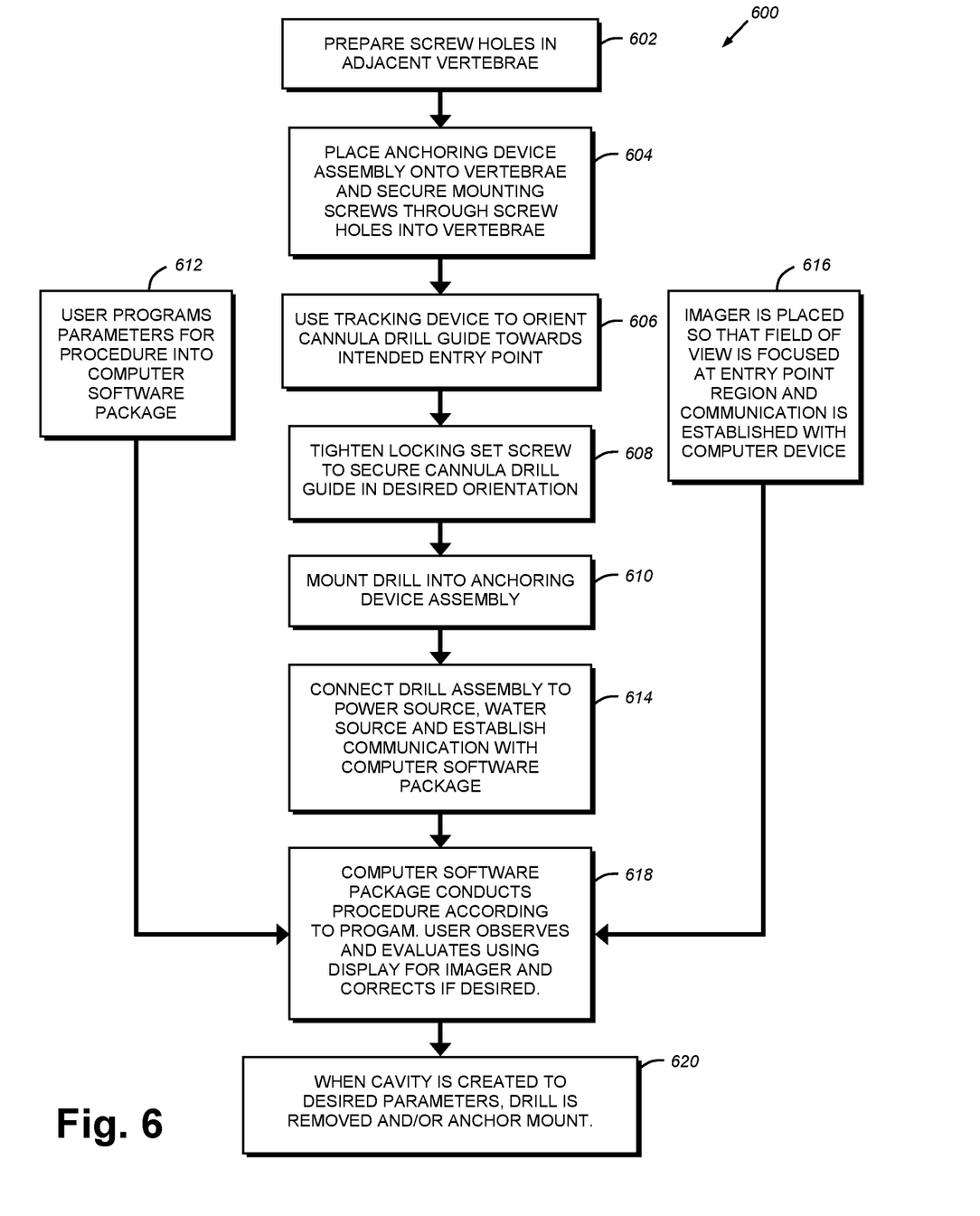
FIG. 6 is a schematic diagram of the steps of a method for cavitation utilizing the anchoring device, according to the illustrative embodiment.

FIG. 6 is a schematic diagram of the steps of a method for cavitation utilizing the anchoring device, according to an illustrative embodiment. By way of non-limiting example, method 600 can be used to create a cavity within a vertebra, but it is specifically contemplated that method 600 can be adapted for use in creating a cavity in a different bone, such as a femur. The user can prepare the location for mounting the anchoring device assembly by creating holes for receiving the mounting screws in two vertebrae adjacent to the vertebrae selected for cavitation in step 602. In an alternate embodiment, the user can prepare the location for mounting the anchoring devise assembly by creating holes for receiving the mounting screws in another bone that is nearby to the targeted entry location, or in a location on the same bone nearby to the targeted entry location. The anchoring device assembly can be placed onto the adjacent vertebrae, or nearby bone, the mounting screws can be inserted through the screw holes in the mounting guide, and the screws can be tightened in step 604. Next, the tracking device can be used to orient and position the cannula drill guide towards the intended entry point in step 606. This can include determining and implementing the desired x, y and/or z-axis settings in the X-Y stage. When the cannula drill guide assembly is satisfactorily positioned, the locking set screw can be tightened to secure the spherical bearing in place in step 608. Next, the drill assembly can be mounted onto the anchoring device assembly by inserting the drill shaft assembly into the cannula drill guide until the distal tip is in proximity to the entry point in step 610. Meanwhile, the user can program into the computer device's computer software package the set of parameters for the cavity creation procedure so as to create a cavity of desired dimensions in step 612. The drill assembly can be connected to a power source and pressurized water source, and communications can be established with the software package in the computer device in step 614. The imager can be placed so that the imager field of view is focused at the entry point and surrounding region and communication between the imager and the computer software package is established in step 616. The user can then activate the computer software package to conduct the drilling procedure to create a cavity according to the set of pre-programmed parameters. The user can observe and evaluate the progress using the displayed images from the imager and the feedback readings from the various sensors on a computer device display in step 618. If intervention and correction of the procedure is indicated by the display and sensors, the user can then revise the procedure until a cavity of the desired dimensions has been created. The drill assembly and/or anchoring device assembly can be removed in step 620. After the cavity is created, the user can then continue the percutaneous vertebroplasty by inserting the medical concrete through the entry point and proceed with the completion of that procedure.

It should be clear to one of ordinary skill that the foregoing provides a system and method for creating a cavity to desired dimensions using a computer guided power drill and that the secure anchor mounting, combined with pre-programmed software, guides the drill so as to optimize the efficacy of the outcome. The secure anchor provides a mounting that minimizes wobbling and vibration in the drill, thereby resulting in a cavity that matches the desired dimension and minimizes potential errors and complications.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, the communications between the various sub-assemblies of the systems can be wired or wireless. The X-Y stage can be manually set or computer driven. The spherical bearing can likewise be motorized and computer-guided. The entire drilling procedure can be remotely viewed by an interface with the display programs of the computer software package for recordation and/or education. Accordingly, this description is meant to be taken only by way of example, and not to otherwise limit the scope of this invention.

What is claimed is:

1. A powered drill for creating a cavity of desired dimensions comprising:
   a drill shaft assembly; and
   a drill motor assembly including a plurality of sensors and a controller unit providing guidance as to rotational speed, motion and depth, wherein the drill shaft assembly includes a drill shaft with an articulating tip that can pivot in a radial arc from a first position that is oriented to a longitudinal axis that is drawn along the shaft to a second position oriented to a perpendicular axis that is perpendicular to the longitudinal axis and a position sensor positioned at a place along the drill shaft.

2. The powered drill of claim 1, wherein the drill motor assembly includes at least one rotational motor that rotationally drives the drill shaft with a rotational spin.

3. The powered drill of claim 1, wherein the drill motor assembly includes at least one linear actuator that provides a back and forth movement of the drill shaft.

4. The powered drill of claim 1, wherein the drill motor assembly includes at least one torque sensor.

5. The powered drill of claim 1, wherein the drill motor assembly includes at least one rotation sensor.

6. The powered drill of claim 1, wherein the drill motor assembly includes at least one electrical resistance sensor.

7. The powered drill of claim 1, wherein the drill motor assembly includes at least one programmable controller unit that includes a plurality of programs that provide a user interface and control the functions and operations of the powered drill arrangement.

8. The powered drill of claim 1, wherein the drill includes a shroud for the drill shaft that includes a port for insertion of water that is pressurized by an external pump for irrigation and removal of deconstructed bone and marrow material from the cavity created by a drilling procedure.

9. The powered drill of claim 1, wherein the drill includes a computer software package that combines user specifications with sensor data to control activation and displacement of the drill.

10. The powered drill of claim 1, wherein the drill includes a computer software package that provides a user interface, controls drill shaft rotational speed and drilling depth.

11. The powered drill of claim 1, wherein the drill includes a computer software package that collects and reports the status of at least one of a position sensor, a torque sensor, a rotation sensor or an electrical sensor.

12. The powered drill of claim 1, wherein the drill includes a computer software package that includes a display that displays status of a drilling procedure.

13. The powered drill of claim 1, wherein the drill includes a computer software package that includes a display for an image from an imaging device that is oriented at a region around a drilling entry point in a bone.

14. The powered drill of claim 1, wherein the drill includes a computer software package that is programmable for a set of parameters for a drilling procedure and that guides the operation of the drill during the drilling procedure.

* * * * *